United States Patent [19]

Ureña

[11] Patent Number: 4,579,529

[45] Date of Patent: Apr. 1, 1986

[54] MANUFACTURING SYSTEM FOR FIXED DENTAL PROSTHESIS

[76] Inventor: Rufino A. Urena, Marqués de Ahumada, 11, Madrid, Spain

[21] Appl. No.: 601,298

[22] Filed: Apr. 17, 1984

[30] Foreign Application Priority Data

Feb. 7, 1984 [ES] Spain .................................... 529533

[51] Int. Cl.$^4$ ............................................ A61C 13/08
[52] U.S. Cl. .................................. 433/208; 433/200.1
[58] Field of Search ............... 433/208, 207, 206, 202, 433/200, 192, 175

[56] References Cited

U.S. PATENT DOCUMENTS

| | | | |
|---|---|---|---|
| 448,745 | 3/1891 | Wright | 433/175 |
| 633,071 | 9/1899 | Campbell | 433/206 |
| 1,501,992 | 7/1924 | Goering | 433/208 |
| 2,778,111 | 1/1957 | Bitter | 433/206 |
| 3,052,982 | 8/1962 | Weinstein | 433/206 |
| 4,059,901 | 11/1977 | Spalten | 433/192 |
| 4,229,170 | 10/1980 | Perez | 433/202 |
| 4,231,740 | 11/1980 | Shoher | 433/208 |
| 4,481,036 | 11/1984 | Panzer | 433/208 |

*Primary Examiner*—John J. Wilson
*Attorney, Agent, or Firm*—Wigman & Cohen

[57] ABSTRACT

The present invention relates to a fixed dental prosthesis having a non-metallic central nucleus, a metallic tube-shaped frame surrounding the nucleus, and an external coating surrounding the frame. The nucleus and coating comprise the same material and are joined together without any discontinuity along the upper and lower edges of the frame in order to define the crown and base of the dental prosthesis. The invention further relates to a system for fixed dental prostheses including a plurality of dental pieces fixed together, each of the dental pieces, including the non-metallic central nucleus, a metallic tube-shaped frame surrounding the nucleus, and an external coating surrounding the frame.

7 Claims, 6 Drawing Figures

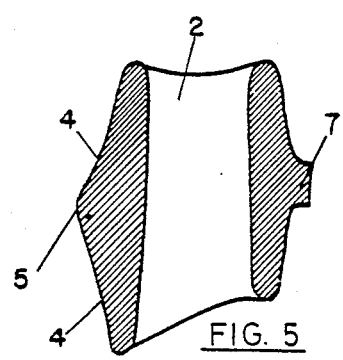
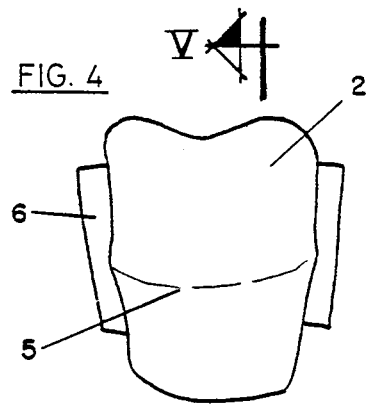
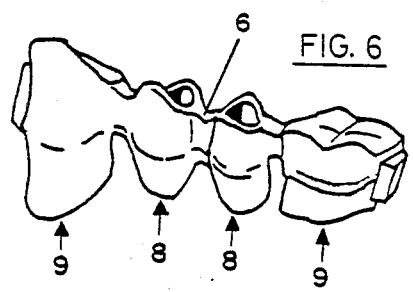

MANUFACTURING SYSTEM FOR FIXED DENTAL PROSTHESIS

This invention relates to a manufacturing system for Fixed Dentral Prosthesis, and more specifically to a manufacturing system of prosthesis consisting of one or more artificial dental pieces, to which extreme sheaths or crowns are attached to be coupled and set over the natural dental pieces restricting the hollow to be filled by such artificial pieces.

Traditionally, artificial dental pieces for such type of prosthesis are made up of a metallic nucleus and a ceramic or acrylic line.

Such constitution of the artificial dental pieces has a number of drawbacks mainly arising from the existence of the solid metallic central nucleus.

Usually, the metal used for the formation of the nucleus is very expensive. The amount of metal required for the formation of the nucleus of each artificial dental piece makes the prosthesis very expensive.

On the other hand, due to the section of the nucleus, during its melting; it is hard to get a uniform and regulated degasification, creating the danger of forming pores inside the nucleus.

As it is known, the coefficient of expansion of the metallic is different than to the nucleus coefficient of expansion of the lining. Accordingly, during the making of the artificial dental pieces, some strains are induced in the lining that might provoke or speed up its breaking, after its placement.

OBJECTS AND SUMMARY OF THE INVENTION

The object of this invention is to develop a manufacturing system of the above type dental prosthesis, making it possible to reduce the manufacturing costs and at the same time to achieve more effective results, both from the point of view of the manufacturing and life of the prosthesis.

According to an object of this invention, the prosthesis artificial dental pieces are made up of a non-metallic central nucleus, a metallic nature, tube-shaped framework surrounding such nucleus and an external lining.

The central nucleus is preferably made-up of the same material as the external lining, both being either ceramic or acrylic in nature. The external lining and the nucleus are joined to each other, without any discontinuance, at the upper and lower edges of the tube-shaped frame, in order to form the crown and base or root of the dental piece.

The tube-shaped frame has a thin wall and has, at least on its external area, some small transverse, projections and hollows, which hollows define anchoring areas for the lining.

Under the described situation, the amount of material to achieve the metallic frame is much lower than the amount used in the traditional systems where there is a solid metallic nucleus. Due to the high cost of such material it may be understood that a price reduction that might be achieved in the manufacturing of the prosthesis under the system of the present invention. At the same time, one succeeds in reducing the full prosthesis weight, thus getting greater comfort for the user or patient.

A further advantage achieved under the system of the invention arises from the reduced thinness of the wall of the tube-shaped frame, in comparison to the section of the metallic nucleus traditionally used until now. Due to the thinness of the wall of the tube-shaped frame, the expansions and contractions due to thermal effects are lower, disappearing practically the expansions and contractions in radial sense and maintaining just those produced in an axial sense.

On the other hand, a greater uniformity may be achieved in the external lining, due to the circumstance that the nucleus of the dental piece, according to the invention, cooperates in setting such ceramic lining. Not being substantial thinness differences in the lining, the danger of creating strains due to thinness difference is eliminated.

Another advantage lies in the possibility of getting a better modelling of the occlusal sides, being able to mould deeper occlusal cavities, due to the fact that such cavities practically match with the nucleus of the dental piece, constituted from the same material of the lining.

In the formation of the tube-shaped frame, there are eliminated in regard to the formation of the traditional solid metallic nucleus, the risks of creation of pores, achieving a more uniform and regulated degasification, all of it due to the thinnesses that is substantially reduced.

The tube-shaped frame shall show in each of the side areas facing the attached dental pieces, a thinner central area crossing through the external filling and being used as joining element for such adjoining pieces.

The mentioned thinner central area crossing through the external filling may peripherally run around the tube-shaped frame, in an angular amplitude of about 180°, between the above mentioned two side areas and over the backward area of the dental piece.

On the other hand, the tube-shaped frame may show free edges substatially in parallel to the free area of the filling in the crown and base of the artificial dental piece.

With the purpose that the manufacturing system of the invention might be better understood, hereinafter a more specific description is being made with reference to the attached drawings, where a possible form of execution is being shown given as an example and not limitatively.

BRIEF DESCRIPTION OF THE DRAWINGS

FIG. 4 is a front elevation view of a frame made according to the invention.

FIG. 5 is a cross-sectional view, taken along line V—V of FIG. 4.

FIG. 6 is a perspective view of a frame completed for a dental prosthesis, formed according to the system of the invention.

DETAILED DESCRIPTION OF A PREFERRED EMBODIMENT

Figure 1:
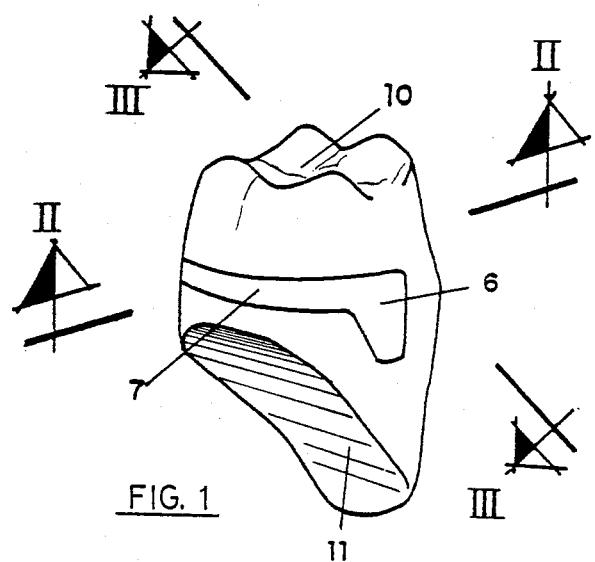
FIG. 1 is a perspective view of the artificial dental piece achieved according to the system of the invention.
Figures 2, 3:
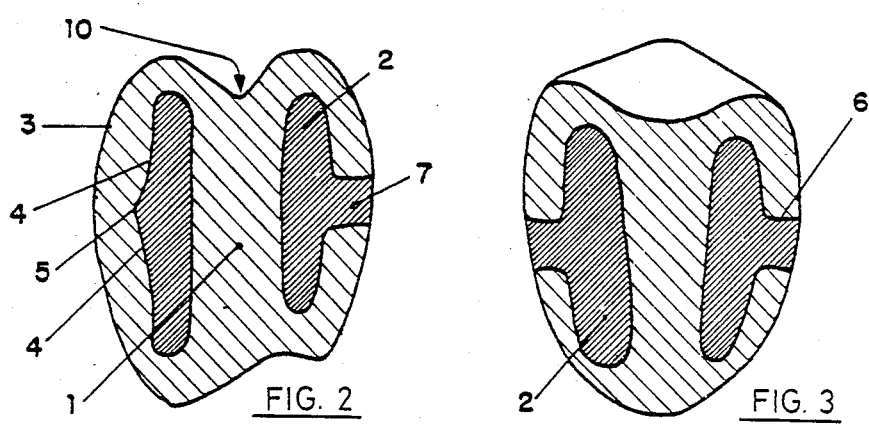
FIG. 2 is a cross-sectional view, taken along line I–II of FIG. 1.
FIG. 3 is a cross-sectional view, taken along line III—III of FIG. 1.

In FIGS. 1, 2 and 3, there is shown an artificial dental piece achieved according to the system of the present invention. Such dental pieces involve a nucleus referenced under number 1, and an external covering 3.

Nucleus 1 and covering 3 shall be preferentially made from the same material, ceramic or acrylic in nature, being attached to each other, without any discontinuity, above and below the edges of the tube-shaped frame 2. The tube-shaped frame 2 is of metallic nature and shall show at least on its external area, some hollows or concavities 4, defined by intermediate transverse projections 5.

In addition, the tube-shaped frame 2 shows, at least in each of the sides areas that shall be facing the joining dental pieces, a thinner central area, that as can be shown on FIG. 1, crosses external covering 3 and acts as joining element for such joined pieces. Such thinner area shall expand preferentially in peripherical sense around the tube-shaped frame in an amplitude about 180°, as can be shown in FIG. 1, according to a band 7, between the thinner side areas 6.

As shown in FIG. 6, areas 6 are for the connection between consecutive frames 8 of dental pieces, and also for joining to the extreme frames 9 of the crowns to be coupled and fixed to the natural pieces.

As clearly shown in FIGS. 2 and 3, by the system of the invention, one gets a better distribution of the covering porcelain or acrylic product, covering the metallic frame almost to the cervical edge. Also a greater uniformity in the thinness of covering 3 is achieved in the whole outline of the pieces.

Due to the existence of nucleus 1, of the same material as covering 3, occlusal cavities 10 may be deeper and with a better moulding of the peaks. Also palatine faces more concave and more anatomic may be achieved. Bases 11 may be achieved with porcelain or acrylic without opaque stripes that could create plaques.

Nucleus 1 of the dental pieces, together with the base and peak thereof, acts as way of rivet from the occlusal, thus getting a safer maintenance of the porcelain.

In the event that joining agents would be required, due to the thinner areas 6 and 7, their use would be restricted to the vestibule area.

Due to the thinness of frame 2, during manufacturing, oxidation and degasification is more uniform and regulated.

On manufacturing of dental pieces, one starts from the knowledge of the dental piece intended to be substituted or replaced. Based on such knowledge, one forms a wax mould corresponding to the wanted configuration for the metallic tube-shaped frame. If the prosthesis involves several pieces, the bridge mould may be prepared unitary with the tube-shaped frame of each piece to be used, as shown in FIG. 6.

By the relevant melting of metallic material, the wax mould is replaced by the metal in the corresponding oven. Following, the controlled form is cooled, finally getting the tube-shaped frames free from damages and occlusions, due to the thinnes of the walls, in addition causing a steady shallow oxidation, with uniform Although only preferred embodiments are specifically illustrated and described herein, it will be appreciated that many modifications and variations of the present invention are possible in light of the above teachings and within the purview of the appended claims without departing from the spirit and intended scope of the invention.

BACKGROUND OF THE INVENTION

The nature of the invention sufficiently described as well as the way to make it in real life, there must be stated that the above mentioned regulations are likely to be modified in detail as far as they do not alter the essential principle.

I claim:

1. A fixed dental prosthesis having a crown and base, comprising:
   a nonmetallic central nucleus;
   a metallic tube-shaped frame having solid walls and being open at the top and bottom surrounding the nucleus;
   an external coating surrounding the frame;
   the nucleus and coating comprising the same material and being joined together without any discontinuity along the upper and lower edges of the frame in order to define the crown and base of the dental prosthesis;
   a central band extending peripherally halfway around the tube-shaped frame and projecting peripherally therefrom;
   wherein the surfaces of the coating at the crown and base are substantially parallel to the free edges of the frame at the crown and base.

2. The prosthesis according to claim 1, wherein the nucleus and coating material is ceramic.

3. The prosthesis according to claim 1, wherein the nucleus and coating material is acrylic.

4. The prosthesis according to claim 1, wherein the frame is thin-walled and has transverse projections and hollows defining anchoring areas for the coating.

5. A system for fixed dental prostheses, comprising a plurality of dental pieces fixed together, each of said pieces comprising:
   a nonmetallic central nucleus;
   a metallic tube-shaped frame having solid walls and being open at the top and bottom surrounding the nucleus;
   an external coating;
   the nucleus and coating comprising the same material and being joined together without any discontinuity along the upper and lower edges of the frame in order to define the crown and base of the dental piece;
   wherein the frame extends through the external coating on each of the side areas facing adjoining dental pieces to attach to the frame of the adjoining dental piece.

6. The system according to claim 5, wherein the surfaces of the coating at the crown and base are substantially parallel to the free edges of the frame at the crown and base.

7. The system according to claim 5, further comprising a central band extending peripherally halfway around the tube-shaped frame and projecting peripherally therefrom.

* * * * *